United States Patent
Haworth et al.

(10) Patent No.: US 9,173,765 B2
(45) Date of Patent: Nov. 3, 2015

(54) JAW THRUST DEVICE AND METHOD

(76) Inventors: Randal Haworth, Los Angeles, CA (US); Corbett W. Stone, San Diego, CA (US)

(*) Notice: Subject to any disclaimer, the term of this patent is extended or adjusted under 35 U.S.C. 154(b) by 357 days.

(21) Appl. No.: 13/443,154

(22) Filed: Apr. 10, 2012

(65) Prior Publication Data

US 2012/0291786 A1 Nov. 22, 2012

Related U.S. Application Data

(62) Division of application No. 12/494,843, filed on Jun. 30, 2009, now Pat. No. 8,191,553.

(60) Provisional application No. 61/076,757, filed on Jun. 30, 2008.

(51) Int. Cl.
| | | |
|---|---|---|
| A61G 15/00 | (2006.01) | |
| A47B 7/02 | (2006.01) | |
| A61F 5/00 | (2006.01) | |
| A61H 5/00 | (2006.01) | |
| A61F 5/055 | (2006.01) | |
| A61F 5/058 | (2006.01) | |
| A61G 13/12 | (2006.01) | |

(52) U.S. Cl.
CPC ............. *A61F 5/055* (2013.01); *A61F 5/05891* (2013.01); *A61G 13/1215* (2013.01)

(58) Field of Classification Search
CPC .................................................. A61G 13/12
USPC .............. 5/637, 630, 636, 640, 643; 128/869, 128/845, 870; 27/13; 602/35, 36, 18, 32, 602/33; 601/39, 41, 42, 43, 44; 297/391
See application file for complete search history.

(56) References Cited

U.S. PATENT DOCUMENTS

| | | | |
|---|---|---|---|
| 1,441,817 A | | 1/1923 | McCullough |
| 1,776,167 A | * | 9/1930 | Stenshoel ...................... 27/21.1 |
| 3,596,655 A | | 8/1971 | Corcoran |
| 4,782,824 A | | 11/1988 | Davies |
| 5,147,287 A | | 9/1992 | Jewell et al. |
| 5,332,287 A | * | 7/1994 | Whitmyer ...................... 297/405 |
| 5,524,639 A | * | 6/1996 | Lanier et al. ...................... 5/630 |
| 5,632,283 A | | 5/1997 | Carden |
| 5,682,632 A | * | 11/1997 | Cotroneo .......................... 5/636 |

(Continued)

OTHER PUBLICATIONS

Deshpande, G., "Mechanical Device for Jaw Thrust and Chin Tilt," NASA Tech Briefs Create the Future Design Contest, presented by SolidWorks, www.createthefuturecontest.com/pages/view/entriesdetail.html?en . . . . , Apr. 25, 2008, pp. 1-2.

(Continued)

*Primary Examiner* — Victoria J Hicks
*Assistant Examiner* — Tarla Patel
(74) *Attorney, Agent, or Firm* — Cermak Nakajima & McGowan; Adam J. Cermak

(57) ABSTRACT

A pair of pads is held against the remus of a patient's jaw, to prevent the jaw from slipping back and causing an airway obstruction, while the patient's neck is hyperextended to also cause the patient's airway to stay open. A device including the adjustable jaw pads as well as a triangularly shaped portion over which the patient's neck rests is not required to be attached to the surface on which the patient is lying, and permits the patient to be rolled on either side while still maintaining the patency of the patient's airway.

8 Claims, 6 Drawing Sheets

(56) References Cited

U.S. PATENT DOCUMENTS

| | | | |
|---|---|---|---|
| 5,791,735 A * | 8/1998 | Helman | 297/407 |
| 6,000,401 A | 12/1999 | Herrick | |
| 6,171,314 B1 | 1/2001 | Rotramel | |
| 6,273,859 B1 | 8/2001 | Remmers et al. | |
| 6,446,288 B1 | 9/2002 | Pi | |
| 6,751,818 B2 | 6/2004 | Troop | |
| 6,969,366 B1 | 11/2005 | Reddick | |
| 7,055,524 B1 | 6/2006 | Taimoorazy | |
| 7,096,869 B1 | 8/2006 | Orlewicz et al. | |
| 7,185,656 B2 | 3/2007 | Wakhloo et al. | |
| 2005/0247309 A1 | 11/2005 | Reddick | |
| 2006/0053557 A1 | 3/2006 | Damron | |
| 2006/0134136 A1 | 6/2006 | Wakhloo et al. | |
| 2007/0118060 A1 | 5/2007 | Gefen et al. | |
| 2010/0062391 A1 | 3/2010 | King | |

OTHER PUBLICATIONS

"LuboCollar Promises an Open Airway," MedGadget, medgadget.com/archives/2007/07/lubocollar_promises_an_open_airway.html, Jul. 26, 2007, pp. 1-5.

Aoyama, K., et al., "New Jaw Support Device and Awake Fiberoptic Intubation," Anesth. Analg. 2000;91:1309-1310, International Anesthesia Research Society.

Napas Airway Management Device, www.beforeyougounder.com/yahoo_site_admin/assets/docs/Napas_Airway_Management_Device.1890252.pdf, pp. 1-6.

International Search Report and Written Opinion for PCT Patent App. No. PCT/US2009/049185 (Aug. 31, 2009).

* cited by examiner

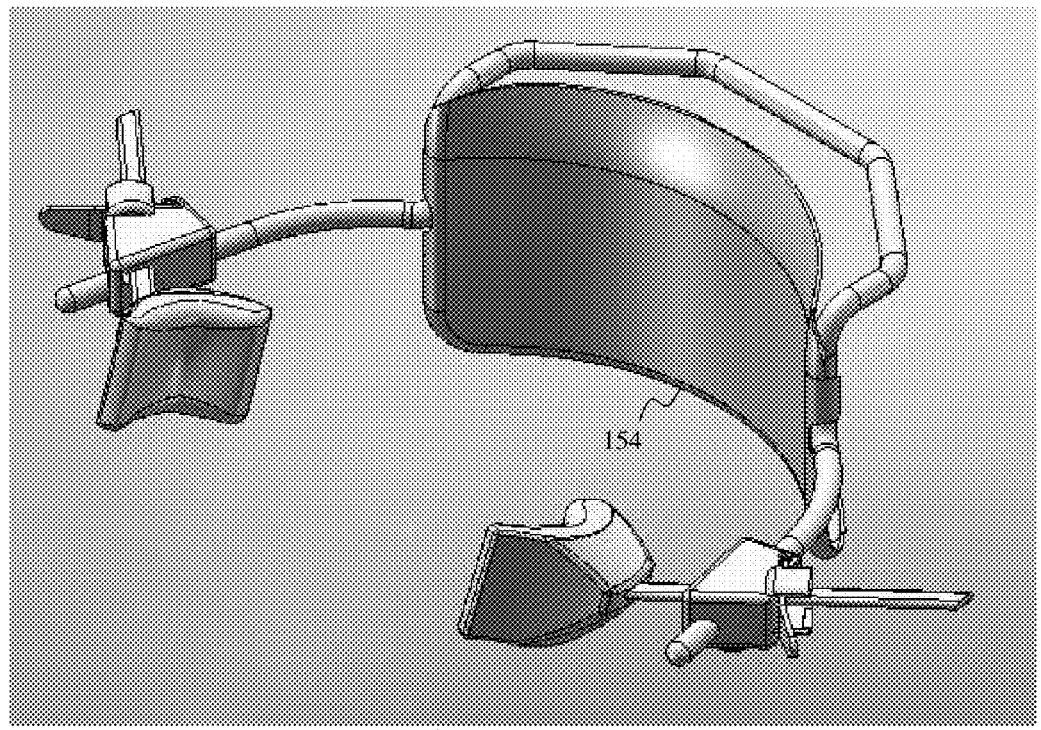
Fig. 9
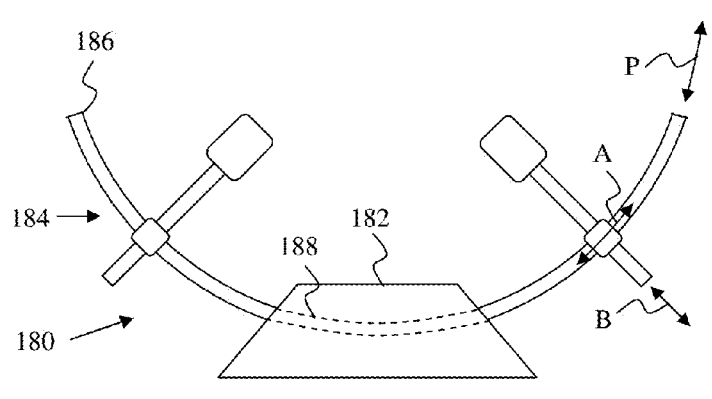 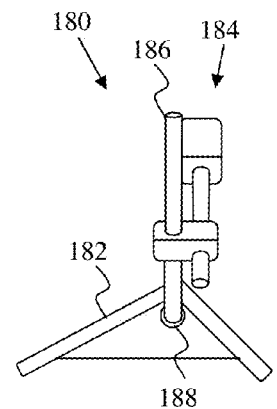
Fig. 10          Fig. 11

JAW THRUST DEVICE AND METHOD

This application is a Divisional of, and claims priority under 35 U.S.C. §120 to, U.S. patent application Ser. No. 12/494,843, filed Jun. 30, 2009 now U.S. Pat. No. 8,191,553, allowed, which claims priority under 35 U.S.C. §119 to U.S. Provisional application No. 61/076,757, filed 30 Jun. 2008, entitled "Jaw Thrust Device and Method", the entireties of which are incorporated by reference herein.

BACKGROUND

1. Field of Endeavor

The present invention relates to devices, systems, and processes useful in patient airway maintenance, and more specifically to devices and methods that perform a jaw thrust.

2. Brief Description of the Related Art

The jaw thrust is a technique used on patients in a supine position to open the patient's trachea (airway), which has become blocked by the backward movement of the lower jaw (mandible) relative to the rest of the patient's skull, which in turn can cause the patient's airway to be blocked. The practitioner typically uses their thumbs to physically push the posterior (back) aspects of the mandible forward and into a position in which the airway is no longer blocked. When the mandible is displaced forward, it pulls the tongue forward and prevents it from blocking (occluding) the entrance to the trachea, helping to ensure a patent (securely unobstructed) airway.

Numerous devices have in the past been proposed for assisting in this procedure, which have been met with limited acceptance. Among the difficulties with prior devices is that many secure the patient's head to the device and/or to the surface (e.g., an operating table) on which the patient is positioned, which limits the medical practitioner's ability to perform procedures on the patient's head and neck. Additionally, many prior devices address only the relative position of the mandible and the associated position of the patient's tongue, and do not address other portions of the patient's airway.

SUMMARY

According to a first aspect of the invention, a jaw thrust device comprises a frame having a pair of upstanding arms with free ends, two jaw pads and two adjustment mechanisms, each of the adjustment mechanisms mounts a respective one of the jaw pads to a respective one of the free ends, and a neck pad positioned on the frame and between the two jaw pads, the neck pad having first and second ends, the frame holding the neck pad first end such that a portion of the frame and the two neck pad ends together form a triangle shape with the neck pad first end at the triangle apex.

According to another aspect of the present invention, a jaw thrust device comprises a frame having a pair of upstanding arms with free ends two L-shaped jaw pads and two adjustment mechanisms, a jaw pad mounted to each arm free end via one adjustment mechanism, and a neck pad positioned on the frame and between the two jaw pads, the frame holding the neck pad.

According to yet another aspect of the present invention, a method for opening a trachea of a patient comprises hyperextending a neck of a patient, and displacing a mandible of the patient anteriorly.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which:

FIG. 9 illustrates a top, right, front perspective view of the embodiment of FIG. 5;

FIG. 10 illustrates a schematic representation of a bottom view of a fifth exemplary embodiment of a device in accordance with the present invention; and FIG. 11 illustrates a schematic representation of a side view of the embodiment of right side of the embodiment of FIG. 10.

DETAILED DESCRIPTION OF EXEMPLARY EMBODIMENTS

Figure 1:
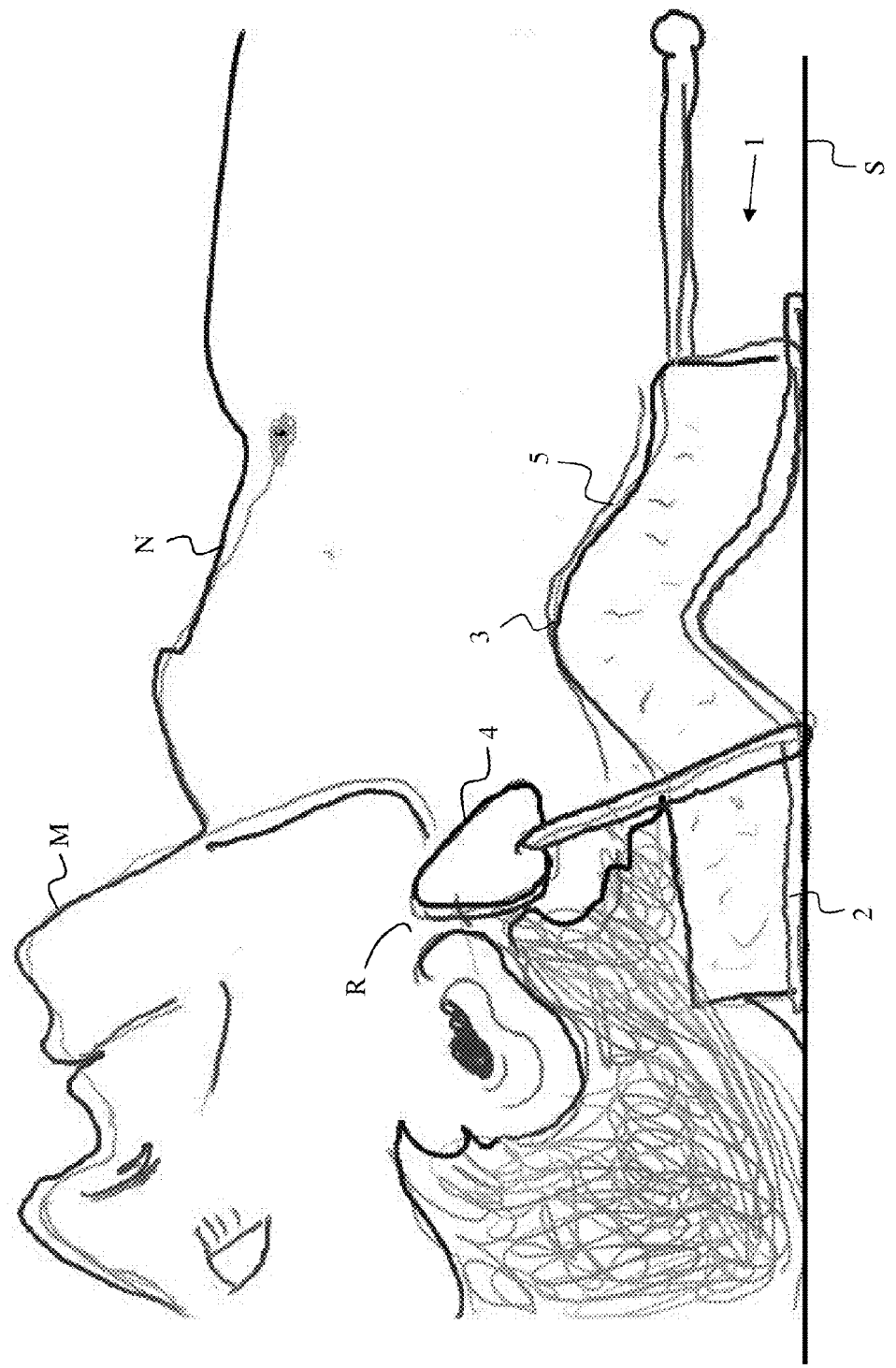
FIG. 1 illustrates an exemplary use of a device in accordance with the present invention to maintain the patency of a patient's airway.

Referring to the drawing figures, like reference numerals designate identical or corresponding elements throughout the several figures.

With reference to FIG. 1, an exemplary device 1 embodying principles of the present invention is illustrated. In FIG. 1, the device 1 is schematically represented. The device 1 can include a base member 2 that can have a generally triangular shape, as see in side profile or sagittal view. The base member 2 can be oriented relative to a support surface S such that an apex 3 of the triangular shaped base member 2 can be positioned at height relative to the support surface S and at least one side 5 of the base member 2 can be inclined relative to the support surface S. When an adult human patient, in a supine position, is positioned on the support surface S with the back of their neck N resting on the base member 2, the angle of the side 5 of the base member 2 and the height of the apex of the base member 2 can cause hyperextension of the patient's neck N. The amount of hyperextension of the patient's neck N can be an appropriate amount sufficient to minimize occlusion of the patient's trachea that may be caused by the patient's internal anatomy.

In order to maintain patency of the patient's trachea once the neck N has been properly hyperextended, the device 1 can include a jaw support 4 secured to the base 2. (Only the right side of the jaw support 4 is viewable in FIG. 4—see FIG. 2, for example, for further illustration of both sides of the exemplary jaw support.) The jaw support 4 can engage and support both sides of the patient's mandible M at a position relative to the apex 3 and the support surface S. In particular, the jaw support 4 can be oriented relative to the patient such that the jaw support 4 engages the ramus portion R on each side of the patient's mandible M. Thus, the jaw support 4 can prevent the patient's mandible M from slipping backwards when the patient's neck N is hyperextended, by the cooperation of inclined side 5 with other features of the base 2, as will be described below.

Figure 2:
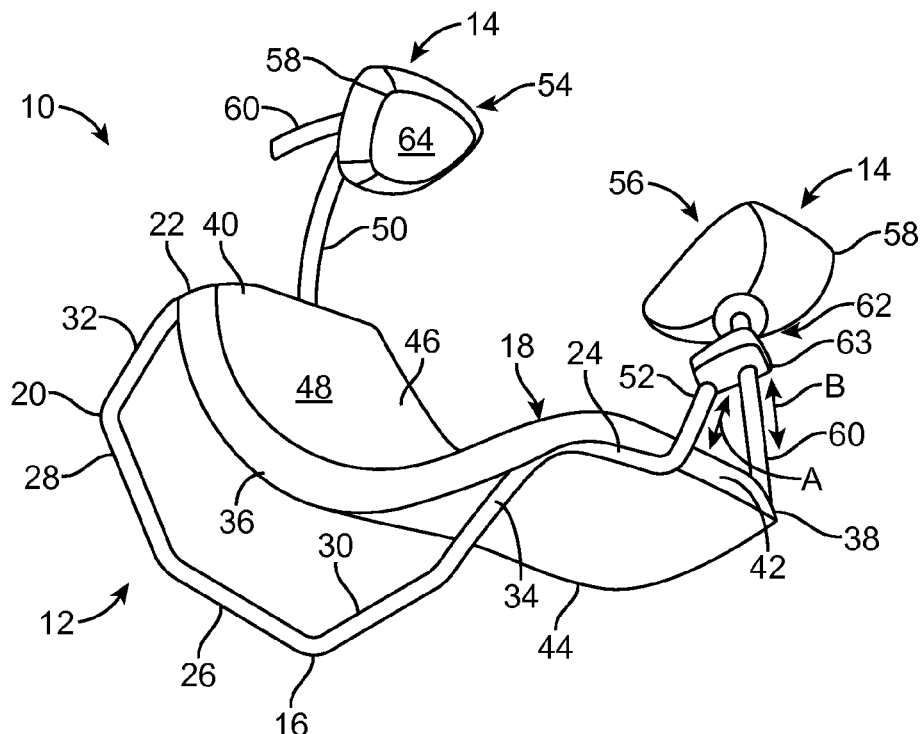
FIG. 2 illustrates a perspective view of a first exemplary embodiment of a device in accordance with the present invention.

A first exemplary embodiment of the device 1 schematically represented in FIG. 1 is shown in FIG. 2. FIG. 2 illustrates a device 10 that can include a base 12 and a jaw support 14 that can engage and support a patient's neck and mandible, respectively, as described above.

The base 12 can include a frame 16 and a neck pad 18. The frame 16 can cooperate with the neck pad to hyperextend the patient's neck an appropriate amount. The jaw support 14 can be connected to the frame 16, as will be described in detail below. The neck pad 18 can be merely placed onto the frame 16 or the neck pad 18 can be positively connected to the frame 16. If the neck pad 18 positively connected to the frame 16, then the neck pad 18 can either be removably connected or permanently connected to the frame 16.

The frame 16 can be configured from a material and with a geometry sufficient to provide an unyielding support of a patent's neck when the patient is lying supine on a support surface. By way of example, the frame 16 can be fabricated from hollow tubing stock or solid rod stock. This stock can have any cross-section deemed appropriate by one skilled in the art. Examples of materials for the stock can include metals and plastics. In another example, stainless steel can be used for the stock material. Stainless steel is a common material for surgical equipment known to for its ability to withstand repeated sterilizations and it can be readily formed into complex geometric configurations.

The frame 16 can form at least a portion of the base 12 and can include a polygonal stand 20, a first pad support 22 (underneath the neck pad 18) and a second pad support 24. The pad supports 22, 24 can extend from opposite ends of the polygonal stand 20. The pad supports 22, 24 can be configured from a material and with a geometry sufficient to provide an unyielding support of a patent's neck when the patient is lying supine on a support surface. By way of example, the pad supports 22, 24 can be fabricated from hollow tubing stock or solid rod stock. This stock can have any cross-section deemed appropriate by one skilled in the art. Examples of materials for the stock can include metals and plastics. In another example, stainless steel can be used for the stock material. Stainless steel is a common material for surgical equipment known to for its ability to withstand repeated sterilizations and it can be readily formed into complex geometric configurations.

The polygonal stand 20 and the pad supports 22, 24 can be integrally formed to define the frame 16 as a single, homogenous component. In this exemplary embodiment, the polygonal stand 20 and the pad supports 22, 24 can be formed by bending the stock into the desired shape. In another exemplary embodiment, the pad supports 22, 24 can be formed as separate components and connected to the frame 20 by any known fastening devices.

The polygonal stand 20 can include a central segment 26, a first lateral segment 28, a second lateral segment 30, a first connector segment 32 and a second connector segment 34.

The first lateral segment 28 can extend from one end of the central segment 26 at an obtuse angle. The second lateral segment 30 can extend from the other end of the central segment 26 at an obtuse angle and symmetrically with respect to the first lateral segment 28. The first connector segment 32 can extend from the first lateral segment 28 to the first pad support 22. The second connector segment 34 can extend from the second lateral segment 30 to the second pad support 24. The first and second connector segments 32, 34 can extend at an obtuse angle relative to the respective first and second lateral segments 28, 30, respectively. The first and second connector segments 32, 34 can extend from the first and second pad supports 22, 24 and any angle deemed sufficient to provide an appropriate hyperextension of the patient's neck. The junction between the first connector segment 32 and the first pad support 22 and the junction between the second connector segment 34 and the second pad support 24 can be arcuate. In another exemplary embodiment, this junction can be angular.

Each of the segments 26, 28, 30, 32, 34 can be integrally formed to define the polygonal stand 20 as a single, homogenous component. Or, each of the segments 26, 28, 30, 32, 34 can be formed as separate components and connected to each other by any known fastening devices to form the polygonal stand 20.

The neck pad 18 can be permanently secured or removably secured to the first and second pad supports 22, 24 in any known manner. If the neck pad 18 is removably connected to the pad supports 22, 24, then the neck pad 18 can be cleaned and reused, or the used neck pad 18 can be disposed and replaced with a new neck pad 18 after each use. The neck pad 18 can span the frame 16 from the first pad support 22 to the second pad support 24.

The neck pad 18 can include a first end 36, a second end 38, a first side 40, a second side 42, a backing 44, and a cushion 46. The cushion 46 can include an engagement surface 48 on a side of the cushion opposite to the backing 44. The backing 44 and the engagement surface 48 can extend from and between the first and second ends 36, 38 and the first and second sides 40, 42. The cushion 46 can be formed as a separate component from the backing 44 and subsequently affixed, permanently or removably, to the backing 44 in any known manner. The backing 44 can have a rigidity sufficient to support the patient's neck in an appropriate hyperextended position above the support surface without substantial deformation to the backing 44. Any known material providing sufficient rigidity can be used to form the backing 44. The cushion 46 can be formed from any known soft, resilient material used for cushions. One example of the cushion material can be a foam material.

The first and second sides 40, 42 of the neck pad 18 can be positioned adjacent to the respective first and second pad supports 22, 24. The first and second sides 40, 42 can extend substantially parallel to the first and second pad supports 22, 24 and can extend beyond the pad supports 22, 24.

The backing 44 can rest against the pad supports 22, 24 without a positive connection thereto. Or, the backing 44 can be positively secured to the pad supports 22, 24 in any known manner. Any positive connection between the backing 44 and the pad supports 22, 24 can be either a removable connection or a permanent connection.

The engagement surface 48 of the neck pad 18 can be generally concave in its extent from the first side 40 to the second side 42. The engagement surface 48 can have a generally convex curvature along a central portion extending from the first end 36 to the second end 38. This compound curvature of the engagement surface 48 can provide stable support in the posterior, inferior, superior, and lateral directions for the patient's neck when the patient's neck is appropriately hyperextended. The backing 44 can mirror the geometry of the engagement surface 48 or the backing 44 can be configured in any suitable geometry.

The first end 36 of the neck pad 18 can be positioned adjacent the junction of the pad supports 22, 24 with their respective connector segments 32, 34. The first end 36 of the neck pad 18 can be spaced from the central segment 26 and the first and second lateral segments 28, 30 of the polygonal stand 20.

The second end 38 of the neck pad 18 can be spaced from the first and second pad supports 22, 24. The second end 38 can curve as it extends from the first side 40 to the second side 42. Alternatively, the second end 38 of the neck pad 18 can be segmented in a manner that corresponds to the central segment 26 and the lateral segments 28, 30 of the polygonal stand 20.

In use, a portion of the second end 38 of the neck pad 18 and a portion of the polygonal stand 20 can be placed on and engage the support surface upon which the patient lies. When placed on the support surface, the engaging portions of the second end 38 and the polygonal stand 20 can define the vertices of a triangular shape, when viewed in profile or sagittal view. The apex of this triangular shape relative to the support surface can lie adjacent the first end 36 of the neck pad 18. The apex of the triangular shape can lie adjacent the junctions of the first and second connector segments 32, 34 with the first and second pad supports 22, 24.

The lengths of the lateral segments 28, 30 and the connector segments 32, 34 of the polygonal stand 20 and the lengths of the sides 40, 42 of the neck pad 18 can be chosen along with the angle defined between the first connector segment 32 and the first pad support 22 and the angle defined between the second connector segment 34 and the second pad support 24 such that the base 12 can elevate the patient's neck above the support surface an amount to appropriately hyperextend the patient's neck. Thus, the frame 16 and the neck pad 18 can cooperate to stably support the neck of a supine patient in an appropriate hyperextended position without the need to fix the device 10 to the support surface.

Routinely, a patient can lie on the support surface in a supine position with both shoulders resting against the support surface. When the engagement surface 48 of the neck pad 18 receives the patient's neck in this supine position, the central segment 26 of the polygonal stand and a central portion of the second end 38 of the neck pad 18 can engage the support surface. In this position, the lateral segments 28, 30 of the polygonal stand 20 can extend away from the support surface. The length of the central segment 26 can be any length sufficient to ensure stable support of the patient's neck while the central segment 26 engages the support surface without fixing the device to the support surface.

However, it may be advantageous to slightly roll the patient toward one side such that the opposite shoulder is slightly spaced above the supporting surface. The device 10 can also support a patient's neck in an appropriate hyperextended position when the patient is slightly rolled toward one side while lying on the support surface. The first and second lateral segments 28, 30 can define beveled corners of the frame 16 that can permit rotation of the base 12 in unison with the patient as the patient is rolled slightly toward one side.

In an instance where the patient is rolled slightly on the support surface toward the patient's left side, the device 10 can be reoriented relative to the support surface in unison with the patient because the device 10 is not fixed to the support surface. When so reoriented, the first lateral segment 28 of the polygonal stand 20 can engage the support surface and the central segment 26 and second lateral segment 30 can be spaced above the support surface.

In an instance where the patient is rolled slightly on the support surface toward the patient's right side, the device 10 can be reoriented relative to the support surface in unison with the patient because the device 10 is not fixed to the support surface. When so reoriented, the second lateral segment 30 can engage the support surface and the central segment 26 and first lateral segment 26 can be spaced above the support surface.

As with the central segment 26, the length of the lateral segments 28, 30 can be any length sufficient to ensure stable support of the patient's neck while the appropriate one of the lateral segments 28, 30 engages the support surface without fixing the device 10 to the support surface. Thus, it is not necessary to fix the device 10 to the support surface when the device is in any of the above-mentioned orientations relative to the support surface. However, the device 10 can be removably fixed relative to the support surface in any known manner, as desired.

In addition to providing stable support of the patient's neck, the concave curvature of the neck pad 18 can accommodate the multiple orientations of the polygonal stand 20 on the support surface. Similarly, the configuration (arcuate or segmented) of the second end 38 of the neck pad can also accommodate the multiple orientations of the polygonal stand 20 on the support surface.

After the patient's neck has been appropriately hyperextended, the jaw support 14 can be used to position the patient's jaw relative to the neck such that occlusion of the patient's trachea by the patient's internal anatomy can be minimized. The jaw support 14 can include first and second mounting arms 50, 52 and first and second jaw pad assemblies 54, 56 engaging the first and second mounting arms 50, 52, respectively.

The first and second mounting arms 50, 52 can extend from the first and second pad supports 22, 24, respectively, at positions external to the first and second sides 40, 42, respectively, of the neck pad 18. Each of the mounting arms 50, 52 can include a first end connected to the respective pad support 22, 24 and a free end spaced from both the pad supports 22, 24. The first ends of the mounting arms 50, 52 can be connected to the first and second pad supports 22, 24 in any manner known in the art suitable to ensure a substantially rigid relationship therebetween.

By way of example, the first and second mounting arms 50, 52 can be fabricated from hollow tubing stock or solid rod stock. This stock can have any cross-section deemed appropriate by one skilled in the art. Examples of materials for the stock can include metals and plastics. In another example, stainless steel can be used for the stock material. Stainless steel is a common material for surgical equipment known to for its ability to withstand repeated sterilizations and it can be readily formed into complex geometric configurations. If the first and second mounting arms 50, 52 are fabricated from the same material stock as the frame 16, then the first and second mounting arms 50, 52 can be integrally formed as a single, homogenous component with the frame 16.

The first and second mounting arms 50, 52 can extend away from the engagement surface 48 to a height sufficient to permit an adjustment range for the respective one of the jaw pad assemblies 54, 56 while not impeding placement of either of the lateral segments 28, 30 onto the support surface. Details of the adjustability offered by the mounting arms 50, 52 will be discussed below.

The first and second mounting arm 50, 52 can be arcuate and can be aligned about a common arc. This geometry can promote contact with the patient's mandible when the neck pad 18 receives the patient's neck. Simultaneously with promotion of contact with the mandible, this geometry imparts a thrust force onto the patient's mandible that can push inward (medially) on the mandible. Thus, the jaw support 14 can be self-seating and can resist slippage relative to the mandible.

The curvature of the mounting arms 50, 52 can also be sufficient to allow clearance of the first and second mounting arms 50, 52 with the support surface when either of the lateral segments 28, 30 of the polygonal stand 20 engage the support surface, as discussed above. The curvature of the first and second mounting arms 50, 52 can also be set to ensure sufficient clearance of the patient's neck as it is moved into and out of contact with the engagement surface 48 of the neck pad 18.

In another exemplary embodiment, the first and second mounting arms 50, 52 can be linear. In another exemplary embodiment, the mounting arms 50, 52 can include an arcuate portion connected to the respective pad support 22, 24 and a linear portion connected to the other end of the arcuate portion.

The second jaw assembly 56 can be substantially identical to or substantially a mirror image of the first jaw assembly 54 and can operate substantially identically to the first jaw assembly 54. Accordingly, the following description of the jaw assemblies 54, 56 will be limited to the second jaw assembly 56.

The second jaw assembly 56 can include a jaw pad 58, an adjustment post 60 and a connector assembly 62. The jaw pad 58 can be secured to one end of the adjustment post 60 in any known manner. The connector assembly 62 can be movably secured to the second mounting arm 52 in either direction indicated by the arrows A. The adjustment post 60 can be movably mounted to the connector assembly 62 in either direction indicated by the arrows B.

The jaw pad 58 can include a deformable core (not shown) and a removable cover. The core can be made from a deformable material and can be secured to the adjustment post 60. The cover can enclose the core in part or in total. The cover can be made from a cloth material and can be removed from around the core for cleaning and reused or the cover can be removed, disposed and replaced with a new cover after each use.

In another exemplary embodiment, the entire jaw pad 58 can be removably mounted to the adjustment post 60. In this exemplary embodiment, the jaw pad 58 can be formed as a single component as compared to a separate core and cover component. This single component jaw pad can be removed, cleaned, and reused. Or, this single component jaw pad can be removed and replaced with a new jaw pad after each use.

The jaw pad 58 can have an engagement surface 64 that can contact the ramus portion of the patient's mandible when the patient is positioned on the device as described herein. In FIG. 2, the engagement surface 64 is best viewed on the jaw pad 58 associated with the first jaw pad assembly 54. FIG. 2 depicts the engagement surface 64 of the jaw pad 60 as a substantially planar surface. However, the engagement surface 64 of the jaw pad 60 can be configured in any geometry deemed appropriate for stable engagement with the patient's mandible.

By way of example, the adjustment post 60 can be fabricated from hollow tubing stock or solid rod stock. This stock can have any cross-section deemed appropriate by one skilled in the art. Examples of materials for the stock can include metals and plastics. In another example, stainless steel can be used for the stock material. Stainless steel is a common material for surgical equipment known to for its ability to withstand repeated sterilizations and it can be readily formed into complex geometric configurations.

The connector assembly 62 can include a housing 63 that can include respective through-holes for the second mounting arm 52 and the adjustment post 60. The connector assembly 62 can slide along the second mounting arm 52 via the respective through-hole and the adjustment post 60 can slide within the respective through-hole of the connector assembly 62. Thus, the first and second jaw pad assemblies 54, 56 can be adjusted to best fit the anatomy of each patient.

The through-hole of the housing 63 that receives the adjustment post 60 can be oriented relative to the base 12 such that the adjustment post extends inwardly and upwardly (superomedially) over the neck pad 18. The adjustment post 60 can slide along its length within the housing 63 so that the jaw pad 58 can engage and subsequently displace the patient's mandible forward (anterior) by an amount sufficient to minimize occlusion of the trachea by the patient's internal anatomy.

Once adjusted to the desired position, the first and second jaw pad assemblies 54, 56 can be fixed in position by the respective connecter assembly 62. By way of example, the connector assembly 62 can include a ratchet assembly (not shown) associated with each of the through-holes. The ratchet assembly can be any known ratchet assembly.

Alternatively, the connector assembly 62 can utilize other fastening devices to secure the second jaw pad assembly 56 relative to the second mounting arm 52 and the adjustment post 60 relative to the connector assembly 62. Examples of these alternate fastening devices can include a set screw, a cam-lever assembly, a ball and detent assembly, etc. In another exemplary embodiment, the through-holes can be dimensioned to provide a friction fit with the mounting arm 52 and the adjustment post 60.

As a independent feature of the jaw pad assemblies 54, 56, the mounting arms 50, 52, adjustment posts 60 and the respective through-holes can have complimentary geometries that can prevent, or at least impede relative rotation between the through holes and the respective one of the mounting arms 50, 52 and the adjustment posts 60. An exemplary geometry can be a square cross-sectional geometry.

Thus, the device 10 can position a patient's neck in an appropriate hyperextended position while the patient lies on the support surface. The device 10 can also be adjusted for each patient so that the patency of the trachea can be maintained after the neck has been hyperextended by an appropriate amount. Additionally, the device 10 can accommodate multiple orientations of the patient relative to the support surface while providing and maintaining the appropriate hyperextension of the patient's neck.

Figure 3:
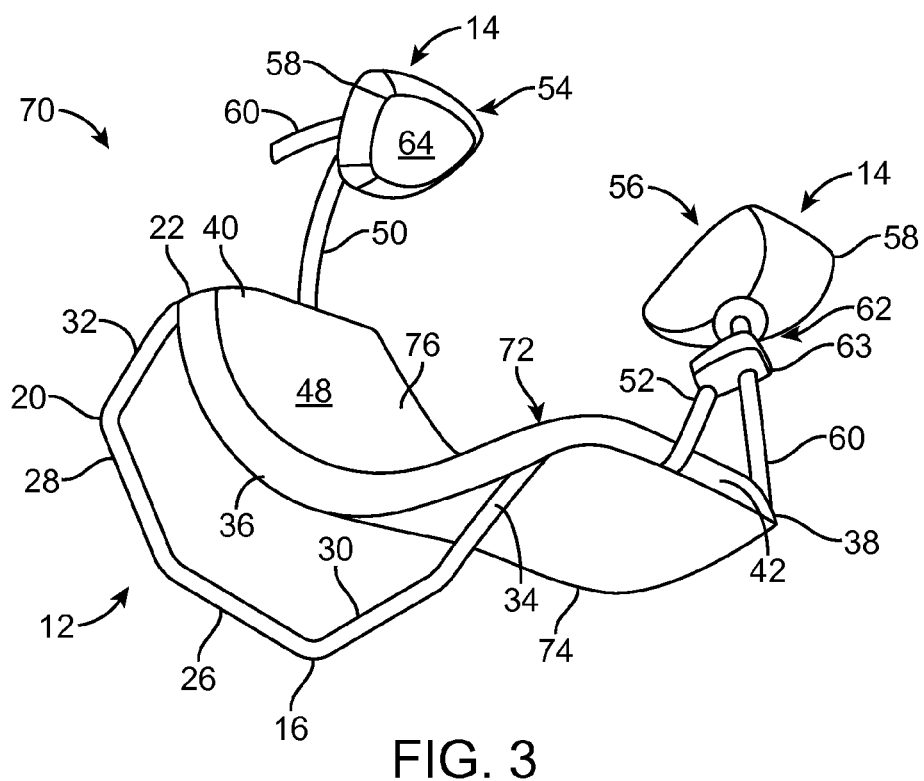
FIG. 3 illustrates a perspective view of a second exemplary embodiment of a device in accordance with the present invention.

FIG. 3 illustrates a second embodiment of the device 1 schematically represent in FIG. 1. In this embodiment, a device 70 can be substantially identical to the device 10 of FIG. 2, except as noted below. Accordingly, substantially identical features of the device 70 are denoted by the same references numerals as used for the device 10 of a FIG. 2.

The device 70 can include a neck pad 72 that can be configured to internally receive the pad supports (not visible—see pad supports 22, 24 of FIG. 2, for example) of the frame 16 and a portion of the mounting arms 50, 52. In particular, the pad supports can extend within the neck pad 72 between the backing 74 and the cushion 76 of the neck pad 72. Thus, the neck pad 72 can be connected to the frame 16.

Figure 4:
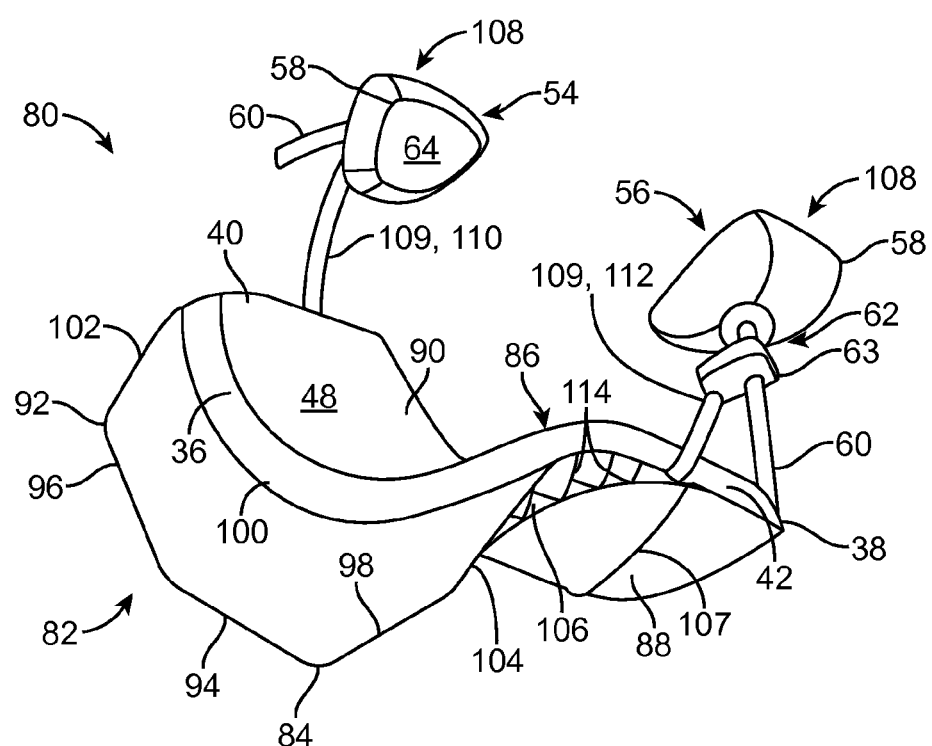
FIG. 4 illustrates a perspective view of a third exemplary embodiment of a device in accordance with the present invention.
Figure 5:
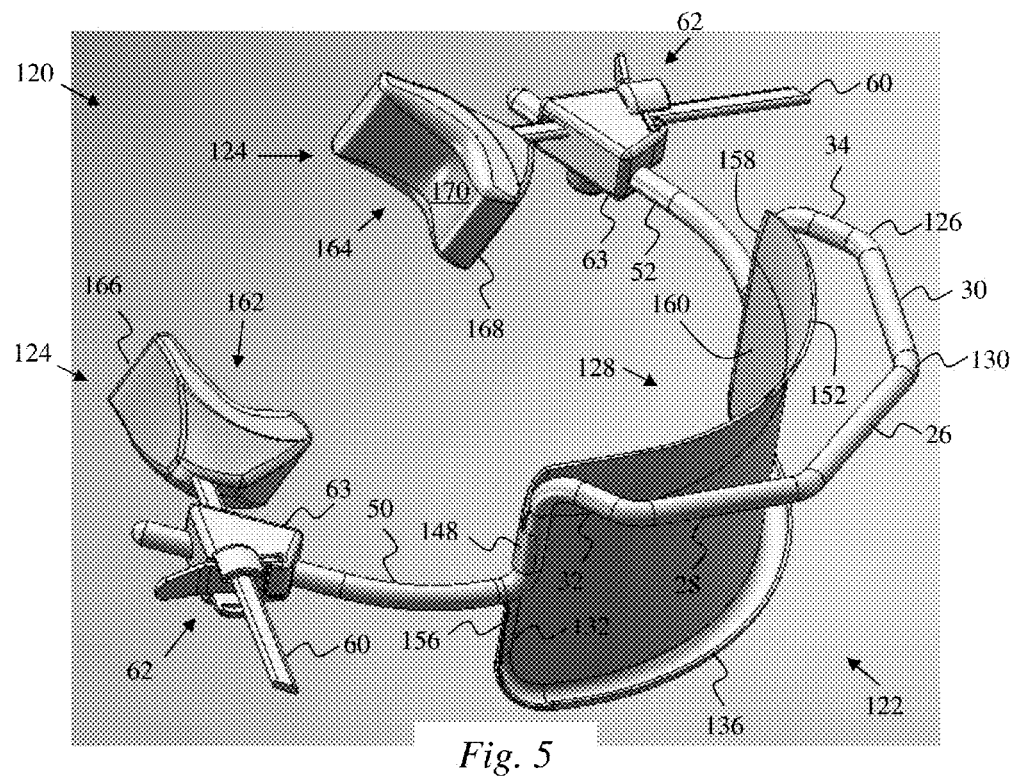
FIG. 5 illustrates a top, right, rear perspective view of a fourth exemplary embodiment of a device in accordance with the present invention.
Figure 6:
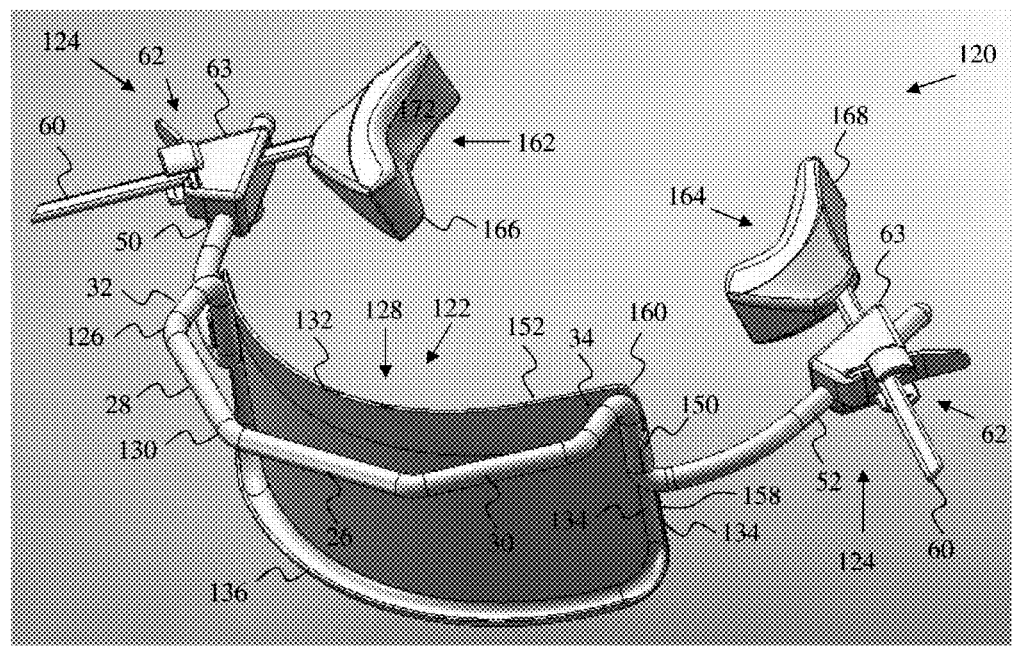
FIG. 6 illustrates a top, left, rear perspective view of the embodiment of FIG. 5.
Figure 7:
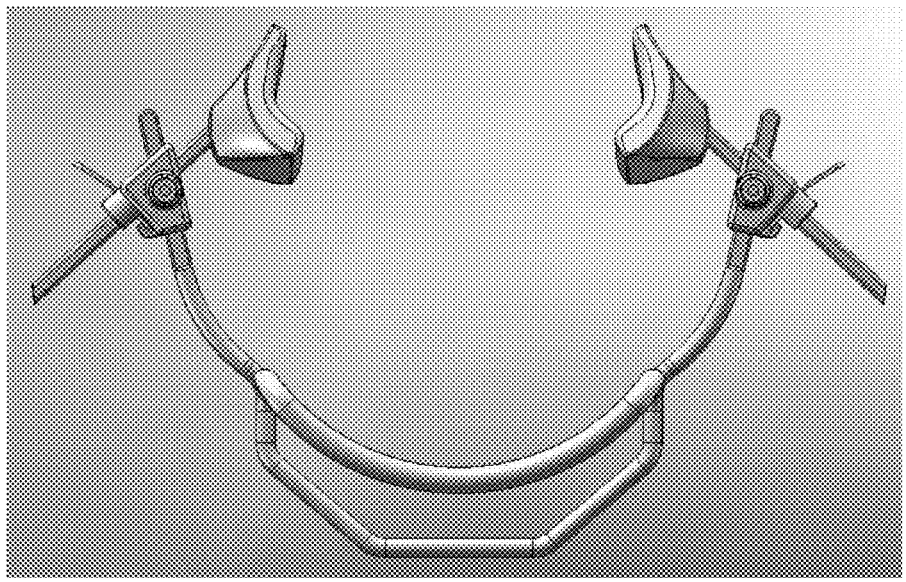
FIG. 7 illustrates a bottom plan view of the embodiment of FIG. 5.
Figure 8:
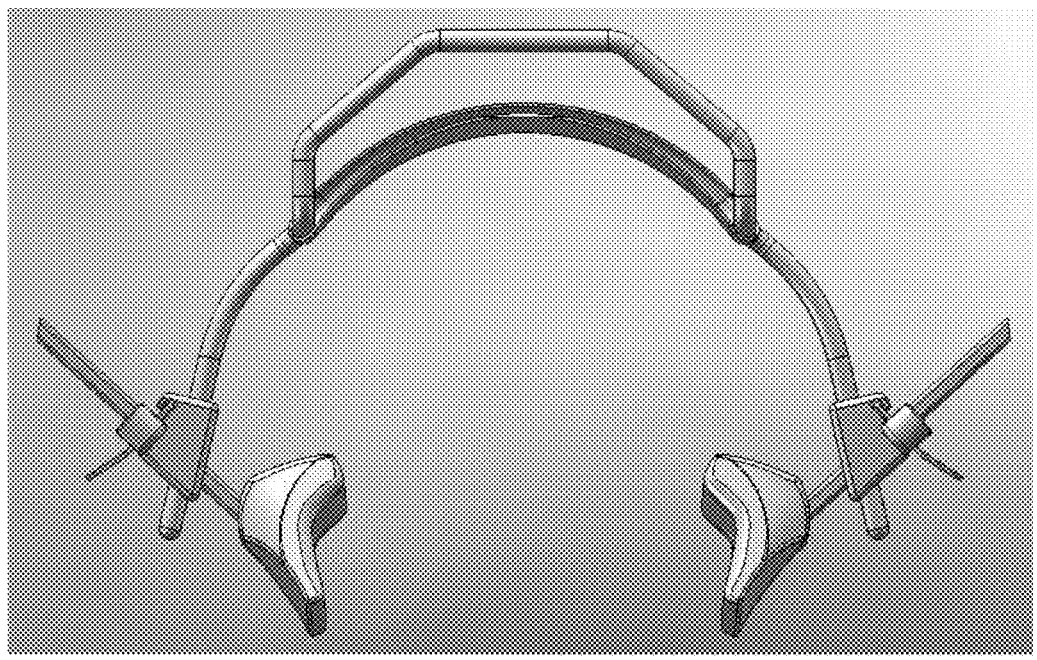
FIG. 8 illustrates a top plan view of the embodiment of FIG. 5.

FIG. 4 illustrates a third embodiment of the device 1 schematically represent in FIG. 1. In this embodiment, a device 80 can be substantially identical to the device 10 of FIG. 2, with any exceptions and/or modifications noted below. Accordingly, substantially identical features of the device 80 are denoted by the same references numerals as used for the device 10 of a FIG. 2.

The device 80 can include a base 82. The base 82 can include a frame 84 and a neck pad 86. The neck pad 86 can include a backing 88 and a cushion 90. The backing 88 and the cushion 90 can include substantially all the features of the backing 44 and the cushion 46 described with reference to the device 10 of FIG. 2. In this exemplary embodiment, the backing 88 of the neck pad 86 can be integrally formed with the frame 84 to define a single, homogenous component. The cushion 90 of the neck pad 86 can be affixed to the backing 88 in any manner described above with reference to FIG. 2.

The frame 82 can include a polygonal stand 92 that can be configured as a solid planar wall. The polygonal stand 92 can include a central edge segment 94, a first lateral edge segment 96, and a second lateral edge segment 98 that lie along the periphery of the polygonal stand 92. The first lateral edge segment 96 can extend from one end of the central edge segment 94 at an obtuse angle. The second lateral edge segment 98 can extend from the other end of the central edge segment 94 at an obtuse angle and symmetrically with respect to the first lateral edge segment 96. The device 80 can be oriented relative to a support surface with any one of the edge segments 94, 96, 98 in contact with the support surface and the remaining edge segments 94, 96, 98 spaced from the support surface in any manner described above with respect the segments 26, 28, 30 of the device 10 of FIG. 2.

The polygonal stand 92 can include an upper edge segment 100, a first side edge segment 102, and a second side edge segment 104. The upper edge 100 can abut the first end 36 of the neck pad 86. The upper edge 100 can be arcuate with a curvature that can conform to the curvature of the first end 36 of the neck pad 86.

The first side edge segment 102 can extend from the first lateral edge segment 96 to the upper edge segment 100. The first side edge 102 can abut the backing 88. The first side edge segment 102 can extend at an obtuse angle relative to the first lateral edge segment 96. The first side edge segment 102 can extend at an acute angle relative to the upper edge segment 100.

The second side edge segment 104 can extend from the second lateral edge segment 98 to the upper edge segment 100. The second side edge segment 104 can abut the backing 88. The second side edge segment 104 can extend at an obtuse angle relative to the second lateral edge segment 98. The second side edge segment 104 can extend at an acute angle relative to the upper edge segment 100.

The edge segments 94, 96, 98, 100, 102, 104 together can define the perimeter of the planar wall of the polygonal stand 92.

The backing 88 can include a groove 107 formed in the surface of the backing 88 that abuts the cushion 90. The groove 107 appears as a convex ridge from the outside of the backing 88, as viewed in the orientation of FIG. 4. The groove 107 can extend from the first side 40 of the neck pad 18 to the second side 42 of the neck pad 90.

The device 80 can include a jaw support 108. The jaw support 108 can include a C-shaped mounting post 109. By way of example, the mounting post 109 can be fabricated from hollow tubing stock or solid rod stock. This stock can have any cross-section deemed appropriate by one skilled in the art. Examples of materials for the stock can include metals and plastics. In another example, stainless steel can be used for the stock material. Stainless steel is a common material for surgical equipment known to for its ability to withstand repeated sterilizations and it can be readily formed into complex geometric configurations.

The mounting post 109 can be centered in the groove 107 such that first and second free ends 110, 112 can extend beyond the respective ends of the groove 107 and the sides 40, 42 of the neck pad 86. The free ends 110, 112 can extend away from the engagement surface 48 of the cushion 90.

The depth of the groove 107 can be such that the mounting post 109 can lie flush with the surface of the backing 88 that abuts the cushion 90.

In an alternate exemplary embodiment, the mounting post 109 can include two separate post sections. In this alternate exemplary embodiment, the groove 107 can include separate groove sections that receive a respective one of the post sections. These separate groove sections can extend from the respective sides 40, 42 of the neck pad 86 and terminate at respective position on the backing 88 intermediate the sides 40, 42.

A further modification for the groove 107 can include a divider spanning the width of the groove 107 that can divide the groove into two sections. Each of these groove sections can receive a respective one of the post sections just described above.

The jaw support 108 can include first and second jaw pad assemblies 54, 56. The jaw assemblies can be substantially identical in structure and operation to the jaw assemblies 54, 56 described above with reference to the device 10 of FIG. 2. The jaw assemblies 54, 56 can be movably mounted along the respective free ends 110, 112 of the mounting post 109.

The frame 84 can further include a first reinforcing support (not visible in FIG. 4) and a second reinforcing support 106. The first reinforcing support can be mirror image of the second reinforcing support 106. Accordingly, further reference is made only to the second reinforcing support 106.

The second reinforcing support 106 can extend from the polygonal stand 92 to the backing 88. The reinforcing support 106 can extend along at least a portion of second side edge segment 104. The second reinforcing support 106 can extend along the bottom surface of the backing 88 and can abut the convex ridge of the groove 107. The second reinforcing support 106 can include a plurality of ribs 114 arranged in a criss-cross pattern. Each of the ribs 114 can span from the bottom surface of the backing 88 to the bottom edge of the reinforcing support 106. The second reinforcing support 106 can provide increased rigidity in the region adjacent the apex of the base 82, where the apex lies adjacent to the junction of the upper edge segment 100 and the first end 36 of the neck pad 86.

The backing 88, the polygonal stand 92, and the reinforcing supports 106 can be formed from any suitable material sufficient to provide an unyielding support of a patent's neck when the patient is lying supine on a support surface. By way of example, the backing 88, the polygonal stand 92 and the reinforcing supports 106 can be fabricated from ABS. However, these components of the device 80 can be formed separately from dissimilar materials. If these components of the device 80 are formed from the same material, these components of the device 80 can be integrally formed to define a single, homogenous component of the device 80.

FIGS. 5-9 illustrate a fourth embodiment of the device 1 schematically represent in FIG. 1. In this embodiment, a device 120 can be substantially identical to the device 10 of FIG. 2, with any exceptions and/or modifications noted below. Description of the device 120 is provided with specific reference to FIGS. 5 and 6.

The device 120 can include a base 122 and a jaw support 124 that can engage and support a patient's neck and mandible, respectively, as described above with reference to the device 10 of FIG. 2.

The base 122 can include a frame 126 and a neck pad 128. The jaw support 124 can be connected to the frame 126, as will be described in detail below. The neck pad 128 can be merely placed onto the frame 126 or the neck pad 128 can be positively connected to the frame 126. If the neck pad 128 is positively connected to the frame 126, then the neck pad 128 can either be removably connected or permanently connected to the frame 126. Details of the engagement of the frame 126 by the neck pad 128 will be described below.

The frame 126 can be configured from a material and with a geometry sufficient to provide an unyielding support of a patent's neck when the patient is lying supine on a support surface. By way of example, the frame 126 can be fabricated from hollow tubing stock or solid rod stock. This stock can have any cross-section deemed appropriate by one skilled in the art. Examples of materials for the stock can include metals and plastics. In another example, stainless steel can be used for the stock material. Stainless steel is a common material for surgical equipment known to for its ability to withstand repeated sterilizations and it can be readily formed into complex geometric configurations.

The frame 126 can include a polygonal stand 130, a first lateral pad support 132, a second lateral pad support 134 and a transverse pad support 136. The pad supports 132, 134 can extend from opposite ends of the polygonal stand 130. The pad supports 132, 134, 136 can be configured from a material and with geometry sufficient to provide an unyielding support of a patent's neck when the patient is lying supine on a support surface. By way of example, the pad supports 132, 134, 136 can be fabricated from hollow tubing stock or solid rod stock. This stock can have any cross-section deemed appropriate by one skilled in the art. Examples of materials for the stock can include metals and plastics. In another example, stainless steel can be used for the stock material. Stainless steel is a common material for surgical equipment known to for its ability to withstand repeated sterilizations and it can be readily formed into complex geometric configurations.

The polygonal stand 130 and the pad supports 132, 134, 136 can be integrally formed to define the frame 126 as a single, homogenous component. In this exemplary embodiment, the polygonal stand 130 and the pad supports 132, 134, 136 can be formed by bending the stock into the desired shape. In another exemplary embodiment, the pad supports 132, 134, 136 can be formed as separate components and connected to the frame 126 by any known fastening device.

The polygonal stand 130 can be substantially identical in structure and operation as described above with reference to the polygonal stand 20 of the device 10 of FIG. 2. Accordingly, reference numbers of FIG. 2 are used in FIGS. 5 and 6 to denote the substantially identical structure of these two embodiments.

The neck pad 128 can be permanently secured or removably secured to the any of the pad supports 132, 134, 136 in any manner known in the art. If the neck pad 128 is removably connected to the pad supports 132, 134, 136, then the neck pad 128 can be cleaned and reused, or the used neck pad 128 can be disposed of and replaced with a new neck pad 128 after each use. The neck pad 128 can span the frame 126 from the first pad support 132 to the second pad support 134.

In this exemplary embodiment, the neck pad 128 can be removably connected to each of the lateral pad supports 132, 134. The neck pad 128 can include first and second clips 148, 150. The clips 148, 150 can be configured to resiliently clamp to a respective one of the lateral pad supports 132, 134.

The neck pad 128 can include a first end 152, a second end 154 (see FIG. 9), a first side 156, a second side 158, a backing 160, and a cushion. The cushion is omitted from FIGS. 5-9 for clarity and can be configured with structure and operation in manner substantially identical to the cushion 46 of the device 10 of FIG. 1. The backing 160 can extend from and between the first and second ends 152, 154 and the first and second sides 156, 158. The pad supports 132, 134, 136 can extend along the entirety of the respective sides 156, 158 and the second end 154. The backing 160 can have a rigidity sufficient to support the patient's neck in an appropriate hyperextended position above the support surface without substantial deformation to the backing 160. Any material providing sufficient rigidity can be used to form the backing 160. According to another exemplary embodiment, the backing 160 alternatively, even if it is less preferable, can be made in the form of a taught sling, that is, of a flexible material that is stretched between the sides.

The structural relationship of the neck pad 128 to the frame 126 can be substantially identical to that described above with respect to the neck pad 18 and the frame 16 of the device 10 of FIG. 1.

The jaw support 124 can be substantially identical in structure and operation to the jaw support 14 of the device of FIG. 2. Accordingly, reference numbers of FIG. 2 are used in FIGS. 5 and 6 and structure that can be unique to the jaw support 124 of the device 120 of FIGS. 5-9, as compared to the jaw support 14 of the device 10 of FIG. 1 will be noted in the following description.

The jaw support 124 can include first and second jaw pad assemblies 162, 164. Reference numbers of FIG. 2 are used to denote structure of the jaw pad assemblies 162, 164 that can be substantially identical in structure and operation as the jaw pad assemblies 54, 56 of the device 10 of FIG. 2.

The jaw pad assemblies 162, 164 can include first and second jaw pads 166, 168, respectively. The jaw pads 166, 168 can be connected to a respective one of the adjustment posts 60 in any manner discussed above with respect to the device 10 of FIG. 2. The jaw pads 166, 168 can include respective L-shaped engagement surface 170, 172. The L-shaped engagement surfaces 170, 172 of the jaw pads can provide a thrust to the lower (inferior edge) of the patient's mandible that can inhibit, and possibly prevent, the patient's mandible from sliding backwards (posteriorly), while also engaging against the side of the patient's mandible along the ramus portion, thus inhibiting, and possibly preventing, the jaw pads 166, 168 from sliding medially into the patient's neck.

FIGS. 10 and 11 schematically illustrate a fifth embodiment of the device 1 schematically represent in FIG. 1. FIGS. 10 and 11 can schematically represent an embodiment of the device 1 substantially identical to the device 80 of FIG. 4. In this embodiment, a device 180 can include a base 182 and a jaw support 184 substantially identical in structure to the base 82 and the jaw mount 14, respectively, of the device 80 of FIG. 4, with at least the following exceptions.

The base 182 can be configured for positive connection to the support surface such that the base 182 can be immobilized relative to the support surface. In this exemplary embodiment, the jaw support 184 is configured to move in either direction along an arcuate path (indicated by the arrows P) relative to the base 182 when the patient is rolled slightly to either side, respectively, while lying supine on the support surface.

The jaw support 182 can include a C-shaped mounting post 186 that can move within an arcuate passage 188 formed though the base 182. The passage 188 can be configured to frictionally engage the mounting post 186 or any known fastening device (not shown) can be used to lock the mounting post 186 in the desired position along the arcuate path P. The passage 188 and the mounting post 186 can be configured with complimentary geometries that can prevent, or at least impede rotation of the mounting post to the left or right, as viewed in FIG. 11. According to yet another exemplary embodiment, similar to that illustrated in FIGS. 10 and 11, the C-shaped mounting post 186 can instead be attached to a platform which is mounted to the base 182. The platform, which includes a triangularly shaped portion which can hyperextend a patient's neck as described with reference to the other embodiments herein, carrying the post 186 and the other affixed structures, slides relative to the base 182 in the same curved path as the post 186 in the embodiment illustrated in FIGS. 10 and 11. In this manner, the patient can be rotated along the same arcuate path P when resting on the platform, keeping the jaw pads pressing against the remus portion of the patient's jaw and pressing against the back of the patient's neck to hyperextend the neck.

As can be readily appreciated from the several illustrations, it can be particularly advantageous when the frame, including the arms, forms at least part of an arc, e.g., a portion of a circle, so that the jaw pads engage the patient's mandible and simultaneously push medially inward on the patient's mandible, thus self-seating the jaw pads to the mandible and resisting the jaw pads slipping off the mandible.

The shape of the head rest also can be advantageous, by effectively forming a 'knee' over which the patient's neck rests, which in turn can provide at least two beneficial effects. The 'knee' of the head rest can stabilize the patient on the device, because the patient's head can rest on the side of the 'knee' opposite the patient's shoulders and lower neck, thus inhibiting, and likely preventing, the device and the patient from sliding relative to each other. Stated somewhat differently, the triangle can provide firm support which can resist any downward movement or disengagement of the neck pad from the neck as the jaw pads are actively thrusting the patient's mandible forward (anteriorly). Additionally, this configuration can hyperextend the patient's neck, which in turn can further assist in opening the patient's airway.

Optionally, for all of the embodiments, a strap (not illustrated) can be provided which can extend around the patient's forehead and around a portion of the device, to assist in holding the device to the patient.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A jaw thrust device comprising:
    a base;
    a pair of upstanding arms with free ends; and
    two jaw pads, a jaw pad mounted to each arm free end;
    wherein the base includes a first lower end, a second lower end spaced longitudinally from the first lower end, and a neck support, the neck support being spaced vertically from a line extending between the first and second lower ends so that the neck support and the first and second lower ends together form a triangle;
    wherein both arms are attached to the base at positions between the first and second lower ends.

2. The jaw thrust device according to claim 1, wherein the neck support is vertically spaced below the jaw pads.

3. The jaw thrust device according to claim 1, wherein the neck support is spaced longitudinally from both of the first and second lower ends.

4. The jaw thrust device according to claim 1, wherein:
    the base includes left and right lateral sides; and
    the base includes a concave portion between the left and right lateral sides.

5. The jaw thrust device according to claim 4, wherein the pads are located vertically above said concave portion.

6. The jaw thrust device according to claim 1, wherein both arms are attached to the base at positions longitudinally spaced from the neck support.

7. The jaw thrust device according to claim 1, further comprising:
    two adjustment mechanisms;
    wherein a jaw pad is mounted to each arm free end via one adjustment mechanism.

8. The jaw thrust device according to claim 1, wherein each jaw pad is movably connected to one of said arms.

* * * * *